US005383366A

United States Patent [19]

Wallingford et al.

[11] Patent Number: 5,383,366

[45] Date of Patent: Jan. 24, 1995

[54] ULTRASONIC TWO PROBE SYSTEM FOR LOCATING AND SIZING

[75] Inventors: Errol E. Wallingford, Sydenham, Canada; Robert DeNale, Arnold, Md.

[73] Assignee: The United States of America as represented by the Secretary of the Navy, Washington, D.C.

[21] Appl. No.: 966,825

[22] Filed: Oct. 26, 1992

[51] Int. Cl.[6] ........................ G01N 9/24; G01N 29/04

[52] U.S. Cl. ........................................ 73/602; 73/624

[58] Field of Search ................. 73/602, 609, 618, 620, 73/624, 627, 628; 128/660.01, 660.07, 660.08, 660.09; 364/506, 507

[56] References Cited

U.S. PATENT DOCUMENTS 4,044,594 8/1977 Owens et al. ..................... 73/67.85
4,435,984 3/1984 Gruber ................................ 73/628
4,441,369 4/1984 Lessard et al. ...................... 73/602
4,570,487 2/1986 Gruber ................................ 73/624
4,682,296 7/1987 Parker ................................ 73/602
4,742,713 5/1988 Abe et al. ............................ 73/620
4,785,667 11/1988 Miyajima et al. .................. 73/618
4,803,638 2/1989 Nottingham et al. ............... 364/507
4,821,574 4/1989 Takamizawa ........................ 73/602
4,821,575 4/1989 Fujikake ............................. 73/626
4,856,336 8/1989 Falkevich et al. ................... 73/598
4,866,614 9/1989 Tam .................................... 73/602
4,869,109 9/1989 Miglianico et al. .................. 73/602
4,878,500 11/1989 Ophir et al. ......................... 73/602
4,908,774 3/1990 Lund et al. ......................... 364/507
4,911,014 3/1990 Lund et al. ........................... 73/602
4,947,351 8/1990 Moran et al. ......................... 73/607

OTHER PUBLICATIONS

M. G. Silk et al., "Ultrasonic Time Domain Measurement of the Depth of Crack-Like Defects in Ferritic and Austenitic Steels", Proceedings of Specialist Meeting on Ultrasonic Inspection of Reactor Components, pp. 1-17, Sep. 1976.

*Primary Examiner*—Richard E. Chilcot, Jr.
*Assistant Examiner*—William L. Oen
*Attorney, Agent, or Firm*—Gary G. Borda

[57] ABSTRACT

A two probe time-of-flight system has a transmit probe emitting a diverging beam into a test material at a certain beam-center angle, and a receive probe with its main beam extending into the test material at that same angle, with the two probes being arranged symmetrical about a centerline normal to the test face. The transmit probe generates a pulse wherein a portion of the pulse reflects at the incident angle back to the receive probe, which detects the reflections and marks the reception time as a reference. A sampling unit captures subsequent echo energy returning from a region within the test material. The sampled energy above a given threshold is processed to identify the sample times relative to the marked reference time. The identified sample times are used to determine the depth that the echo energy originated from. Consecutive identified samples in the depth direction are used to detect the height of a flaw within the test material. By scanning the probes in an x-y pattern, the planar dimensions of the flaw are determined.

14 Claims, 11 Drawing Sheets

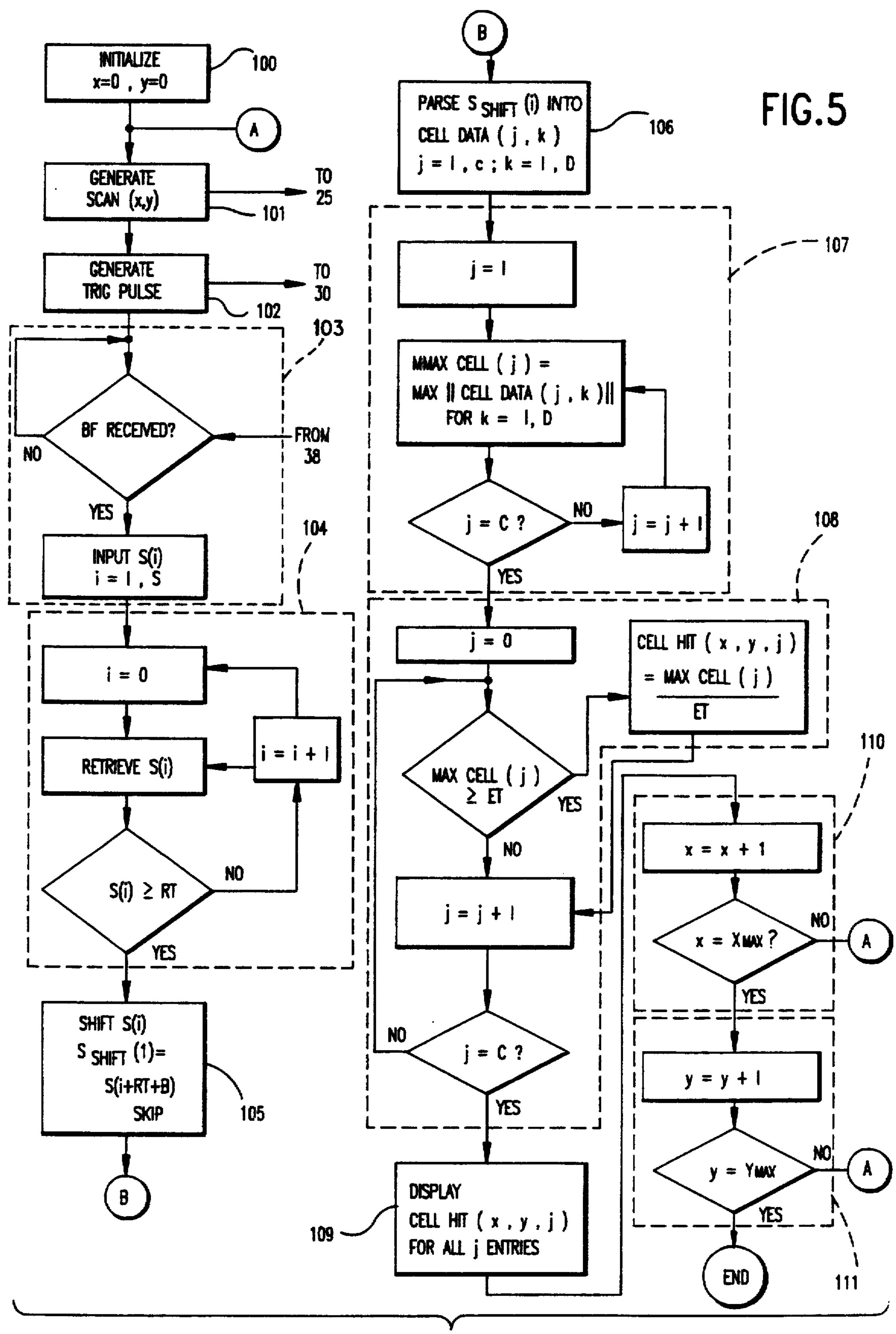

FIG.5
INITIALIZE x=0 , y=0
100
A
GENERATE SCAN (x,y)
TO 25
101
GENERATE TRIG PULSE
TO 30
102
103
BF RECEIVED?
FROM 38
NO
YES
INPUT S(i) i = 1 , S
104
i = 0
RETRIEVE S(i)
i = i + 1
S(i) ≥ RT
NO
YES
SHIFT S(i) S SHIFT (1)= S(i+RT+B) SKIP
105
B
B
PARSE S SHIFT (i) INTO CELL DATA ( j , k ) j = 1 , c ; k = 1 , D
106
107
j = 1
MMAX CELL ( j ) = MAX ‖ CELL DATA ( j , k )‖ FOR k = 1, D
j = C ?
NO
j = j + 1
YES
108
j = 0
CELL HIT ( x , y , j ) = MAX CELL ( j ) / ET
MAX CELL ( j ) ≥ ET
YES
NO
j = j + 1
j = C ?
NO
YES
DISPLAY CELL HIT ( x , y , j ) FOR ALL j ENTRIES
109
110
x = x + 1
x = XMAX ?
NO
A
YES
y = y + 1
y = YMAX
NO
A
YES
END
111

ULTRASONIC TWO PROBE SYSTEM FOR LOCATING AND SIZING

BACKGROUND OF THE INVENTION

1. Field of the Invention

The present invention relates generally to a non-destructive detection and three dimensional sizing of subsurface flaws within a solid material and has particular applicability, but is not limited to, a detection of flaws within a metal weld.

2. Description of the Prior Art

There are two general non-destructive methods in the prior art for detecting subsurface flaws in a solid material, these being X-ray radiography detection and ultrasonic detection. The present invention relates to ultrasonic detection.

One prior art method of ultrasonic detection of flaws within a solid material is a single probe, "pulse echo", method.

Basically, the single probe pulse echo operates by emitting, from a transmit/receive probe, an ultrasound pulse and then monitoring the received echo for any pulses received which are above a set threshold value. The echo pulses are the reflections from the discontinuities surrounding any subsurface flaws. Based on the time delay of recovery of the flaw echo, the depth to the first major discontinuity of the flaw can be calculated. By scanning the probe along the test surface direction, the length of the flaw is indicated by the relative positions along the scan where its echo first appears and where the echo vanishes. However, a substantial shortcoming of the single probe pulse echo method is that it cannot accurately determine the height of the flaw. The reason, as best theorized by the present inventors is as follows: When the incident sound pulse travels downward into the test material and strikes a discontinuity at the upper portion of a first flaw there is a reflection back from that discontinuity. The single probe pulse echo method, by its usual operation, measures the time of receiving this reflection and, based on the known height of the probe above the surface and the speed of sound through the material, calculates the depth of the discontinuity, and hence the upper portion of that first flaw. Since there is a discontinuity at the lower portion of the same flaw then, in theory, if the single probe method could detect a reflection from that portion then the height of the flaw could be determined. However, this is not practicable. The main reason is that the upward reflection from that lower portion will itself be perturbed by the discontinuity at the upper portion of the flaw. In other words, the upper portion of the flaw interferes with echoes from the lower portions of the same flaw. Furthermore, because of the longer path length through the material to the lower discontinuity, that lower reflection will be of a significantly lower amplitude than the upper reflection. Since the system must detect flaws of varying depth, but not be overwhelmed by extraneous noise, the detection threshold cannot be set low enough to detect these signals. For a similar reason, when there are multiple flaws, one overlaying another, the upper flaw interferes with detection of echoes from the lower flaw. Therefore the lower flaw is not detected. Also, since the amplitude of the reflection echo is dependent on the angular orientation of the flaw, the single probe pulse echo method is prone to miss the detection of unfavorably oriented flaws, particularly those of smaller size.

There are two types of two probe methods shown in the prior art. The first is referred to as the transmission method. This method utilizes two transducers with the material under inspection being inserted between the two. An ultrasonic energy is launched from one of the transducers, propagates through the material and the intensities of the received pulses are measured by the receiving transducer on the other side. As long as a signal is received the material is considered to be defect free. A defect, on the other hand, reflects a significant portion of the propagating pulse and caused a loss of signal at the receiving transducer. This method, of course, is limited to situations where both sides of the tested material are accessible. Also it cannot readily measure defect depth. The other method, which is discussed in an article by M. G. Silk et al., "Ultrasonic Time-Domain Measurements of the Depth of Crack Like Defects in Ferritic and Austenitic Steels", *Proceedings of Specialist Meeting on Ultrasonic Inspection of Reactor Components*, pp. 1-17, September 1976, is termed the Time-of-Flight Diffraction Method. In this method, two transducers are arranged on the same side of a material, separated by a short distance. According to Silk, sound insonifies the material being inspected and at the same time produces what is termed as a "lateral wave" just below the surface of the material. The lateral wave provides a timing reference for subsequent signals diffracted from subsurface defects. However, no physical mechanism can be found for generating a surface wave in a solid medium from a liquid medium, especially with the incident wave in the liquid medium being nearly normal to the surface of the solid, as taught by Silk. The lack of a surface wave, in conjunction with other sonic effects inherent with the transducer arrangement taught by Silk, as well as the sonic model used for the subsequent calculations, result in that method having limited depth measurement accuracy and fault detection performance.

SUMMARY OF THE INVENTION

The first object of the present invention is a practical method and apparatus for detection and three dimensional characterization of a flaw within a solid material. This object is achieved by providing an apparatus and method to measure the height of a flaw, which the above-discussed prior art methods cannot perform, in addition to the flaw's planar dimension and depth.

The second object of the present invention is to provide for detection of each of a plurality of overlapping flaws, including a flaw lying completely beneath another.

The third object of the present invention is to substantially eliminate the effect of flaw orientation on the detectability.

A fourth object is to substantially reduce the amplitude range of echoes received from flaws, even between flaws of varying depth and orientation. This in turn allows a narrowed flaw echo qualifying window compared with prior art methods. Further objects can be achieved by this reduced range of amplitudes, which include data reduction, by only passing echoes within the narrow window for processing, and an increased signal-to-noise ratio by excluding unqualified amplitudes.

A discovery underlying the present invention is that by positioning the transmit probe to emit a diverging beam into a test material at a certain beamcenter angle, and by placing a receive probe with its main beam extending into the test material at that same angle, with the two probes being arranged symmetrical about a centerline normal to the test face, that three unexpected results are obtained. The first is that reflection echoes from similarly dimensioned flaws at different depths share a common amplitude when they arrive at the receive probe. Included with this result is that echoes from the upper and lower portions of the same flaw have the same amplitude. This first benefit appears to result from the different angle that the incident beam strikes an upper flaw surface as compared with the angle that it strikes a lower flaw surface. These differing angles are caused, using the two probe arrangement of the present invention, by the divergence of the incident beam at the respective depths within the test material. It appears that the angle of incidence at the upper flaw surface results in an echo with a lower amplitude component in the direction of the receive probe beam than an echo results from the angle of incidence at the lower flaw surface. As theorized by the present inventors, the larger amplitude echo from the lower flaw surface substantially cancels the greater attenuation encountered by this echo. Therefore, even though the lower flaw echo has a greater attenuation from its longer propagation path than the upper flaw echo, the two echoes will strike the receive probe with substantially the same amplitude.

The second benefit resulting from the two probe arrangement of the present invention is that the deeper of any two overlaying flaws can be detected. The reason results from the relative positioning of the transmit and receive beam angles, whereby the echo path from the lower flaw is not interfered with by the upper flaw. Included with this second benefit is that echoes from lower portions of a flaw do not encounter interference from upper portions of the same flaw. Therefore, as will become obvious from the detailed description following, echoes from the lower flaws of overlaying flaws and echoes from lower surfaces of the same flaw can be detected.

In accordance with this discovery, the present invention achieves the above objects, and others which will become apparent from the detailed description following, by a two probe method and apparatus which includes the operative steps of generating an ultrasonic pulse, at a pulse reference time, towards a surface of a material under test, with the pulse incident to the surface along a main generating beam of a transmitting probe at an angle $\Theta$. Receiving a reflected ultrasound energy along a main receiving beam of a receiving probe, displaced from the transmit probe a predetermined distance parallel to the test surface, wherein the receiving probe is positioned so that its main receiving beam has an included angle of approximately $2\times\Theta$ with the main generating beam of the transmitting probe. Sampling the receiving probe output over a predetermined time window relative to the time of the pulse generation (i.e., pulse reference time) and outputting a sample data stream. Storing scan data, consisting of a series of consecutive datum from the sample data stream sampled over a predetermined time interval, and generating index data to identify the respective times of sampling of the scan data. Processing the stored scan data to detect which of the datum has an energy correlating to a prestored surface reflection threshold value. The time of sampling the first surface is then known by the reference index of the detected datum, which is identified as the reference datum. Further processing the stored scan data to identify the index position, and hence the relative time of sampling, of data points having characteristics which correlate with a predetermined flaw echo threshold value. Based on the difference between the indexes of the data identified as correlating with the flaw echo threshold value and the index of the reference datum, the time-of-flight difference between the sampling time of each of these identified datum points and the sampling time of the reference data is known. Finally, outputting the index differences as depth cell data. The depth cell data can be converted into an actual depth dimension of a discontinuity within the test material by a time-of-flight model equation which is based on the position of the transmit and receive probes, the angle and geometry of their respective beam paths towards the test surface, and the speed of sound propagation through the test material and the medium through which the two probe beams extend toward the test material. Values for the time-of-flight equation can be prestored so that the depth cell data can be mapped to a depth dimension.

In addition, the present invention may calculate a correlation between datum points within the depth cell data and, based on the correlation, output height datum estimation of the height of a three dimensional discontinuity within the test material.

Furthermore, the present invention may displace the main generating beam and the receiving beam a predetermined distance in a first direction parallel to the test material surface. Second depth cell data is then generated with the two probes at this displaced position. The second depth cell data is then correlated against the depth cell data obtained at the predisplacement position and correlation data is output accordingly. Based on this correlation data, a planar dimension datum is output corresponding to a dimension along the first displacement direction of a discontinuity within the test material.

Still furthermore, the present invention may, based on a low correlation between different datum from within the depth data, delete one or more of the different datum.

Still furthermore, the present invention may display the depth cell data in a manner indicative of the planar dimensions, the depth, and the height of a discontinuity within the test material.

BRIEF DESCRIPTION OF THE DRAWINGS

FIG. 5 is a software flow chart showing the control and data processing flow within an automated weld flaw detection system according to the present invention.

DETAILED DESCRIPTION OF THE PREFERRED EMBODIMENTS

The present invention can be assembled, with the exception of a special probe holder which will be described in detail, entirely from, and is described here in reference to, off-the-shelf hardware.

First Embodiment

The description of the operation of the present invention will be made in reference to FIGS. 1-3. This first embodiment will describe the general operation of the present invention, while optional and alternate features will be explained in the further embodiments.

Figure 2A:
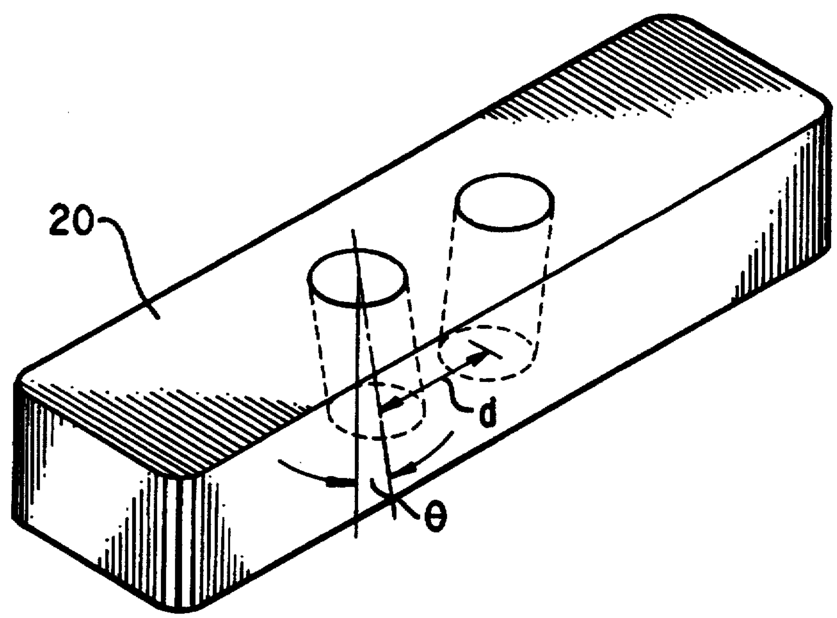
FIG. 2A and FIG. 2B shows a two probe holder having optimized dimensions according to one aspect of the present invention.
Figure 2B:
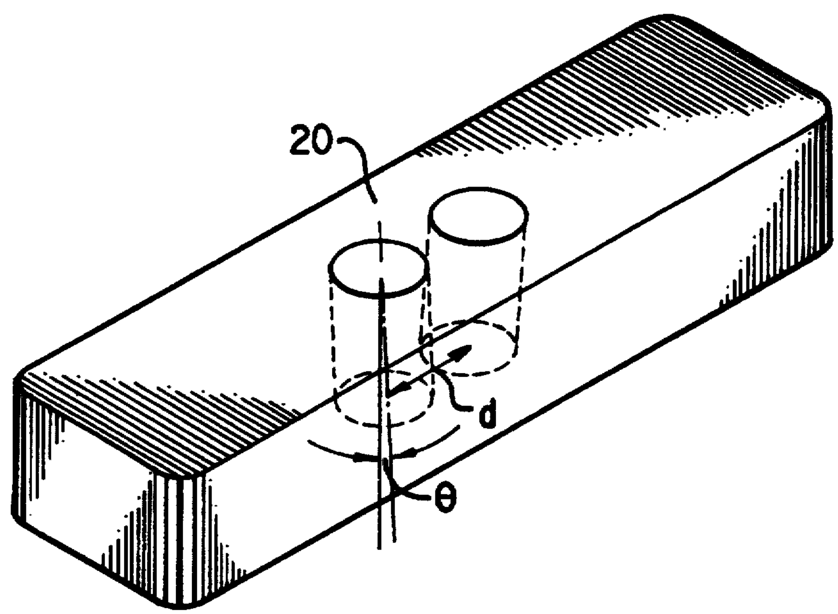
Figure 3:
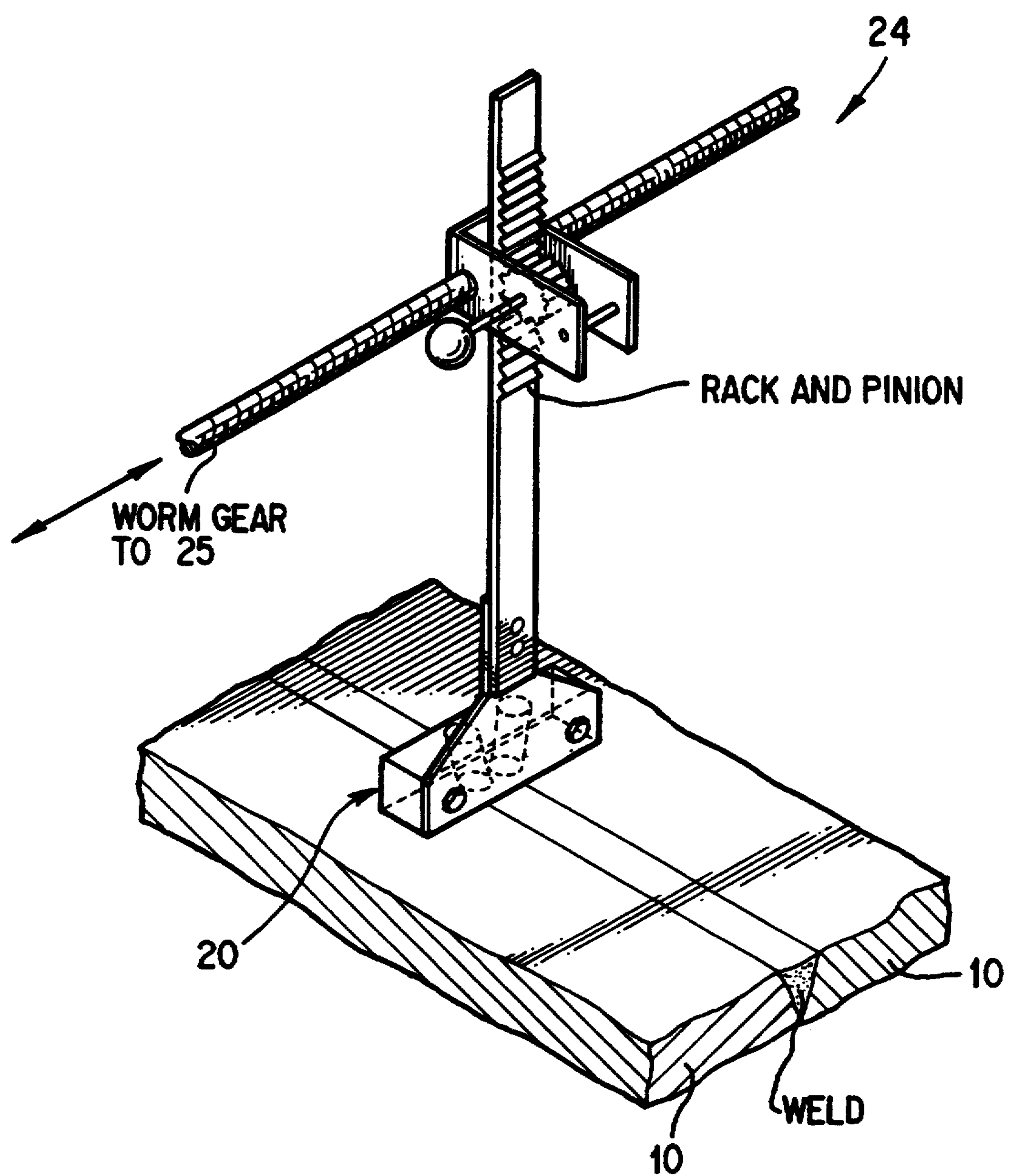
FIG. 3 shows an x-y scanner support for a two probe holder according to one aspect of the present invention.
Figure 4:
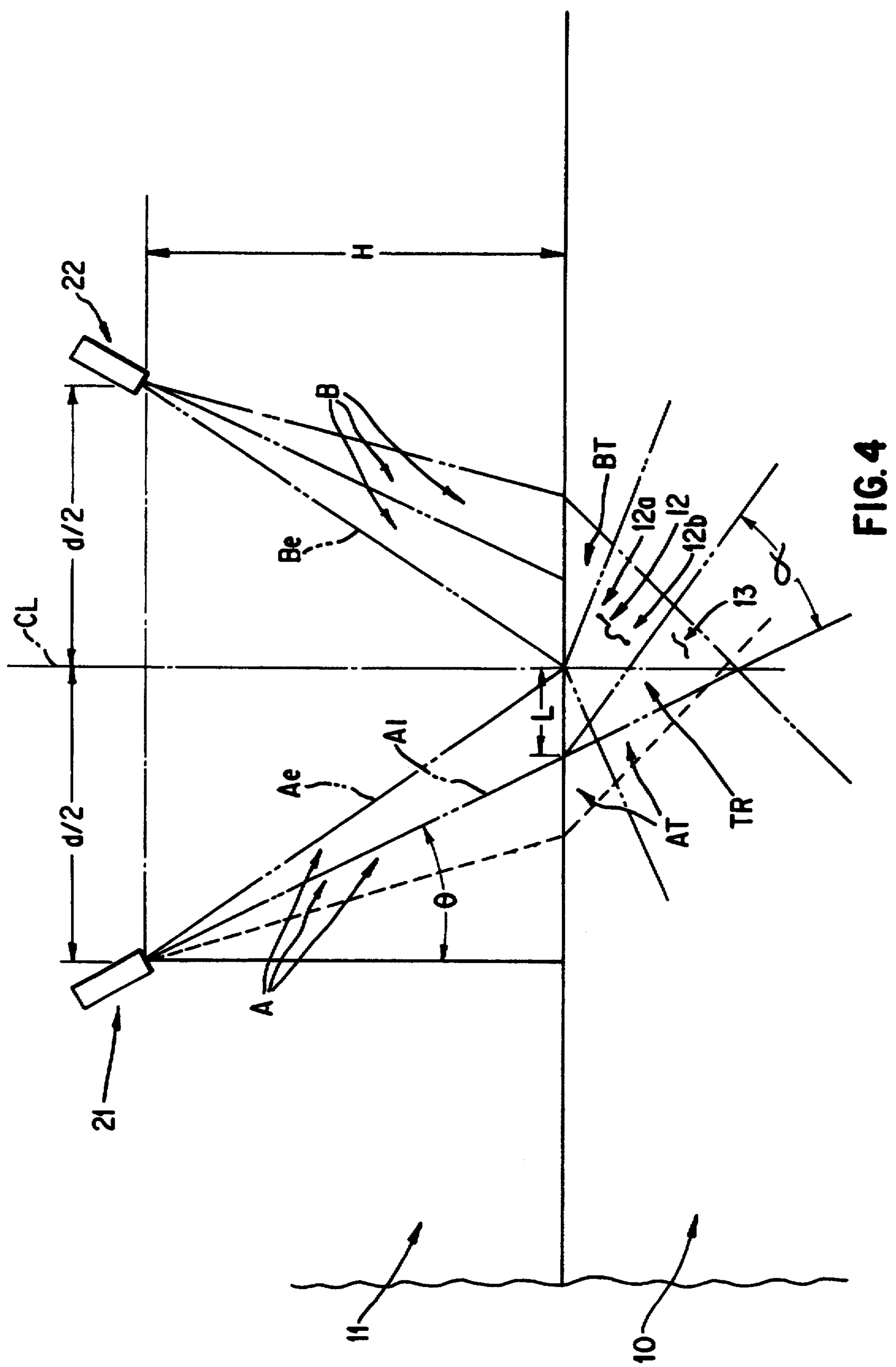
FIG. 4 is a diagram of the mathematical model of the sonic wave paths, media boundaries, and relevant parameters thereof used by the present invention, to which reference will be made in explaining the operation of the present method and apparatus.

FIG. 4 shows a material 10 to be tested for subsurface flaws and a medium 11 in which the test probe holder 20 of FIG. 2 is positioned. The test probe holder 20 securely mounts a transmit probe 21 and a receive probe 22 such that each is at a distance d/2 from their mutual centerline CL. The probes 21 and 22 must be supported within the holder 20 so as to be tilted at an angle Θ towards each other. For reasons explained below, the distance d/2 and the angle Θ can be optimized according to the material to be tested and the particular range of depths to be scanned. The holder 20 is supported above the surface of the test material 10 by a support 24, an example of which is shown in FIG. 3. The support 24 maintains the probes 21 and 22 at a height H above the surface of the test material 10. H is selected, as explained below, so as to place the surface of the test material 10 in the far field of the probes 21 and 22. In this embodiment, the support 24 is a ratchet assembly, so as to raise and lower the probes 21 and 22. Alternatives include a carriage type assembly, as described in U.S. Pat. No. 4,044,594, or a solid perspex block. To facilitate automated flaw scanning, the support 24 is attached to an xy scanner 25, such as a Velmex XY Scanner, which moves the probes 21 and 22 via a command signal Scan(x,y) output from the system computer 32 over its RS-232 port. The computer 32 can be an IBM AT type, such as a Zenith Model 248. Alternately, for manual scanning, a manually moveable version (not shown) of the xy-scanner 25 could be used, having means (not shown) to output x,y signals (not shown) to the computer 32 to indicate the x-y position of the support 24. The computer 32 is connected, via its standard printer output port, to a general purpose printer 62. The printer 62 for this embodiment is an Alps Model P2000G.

Figure 1:
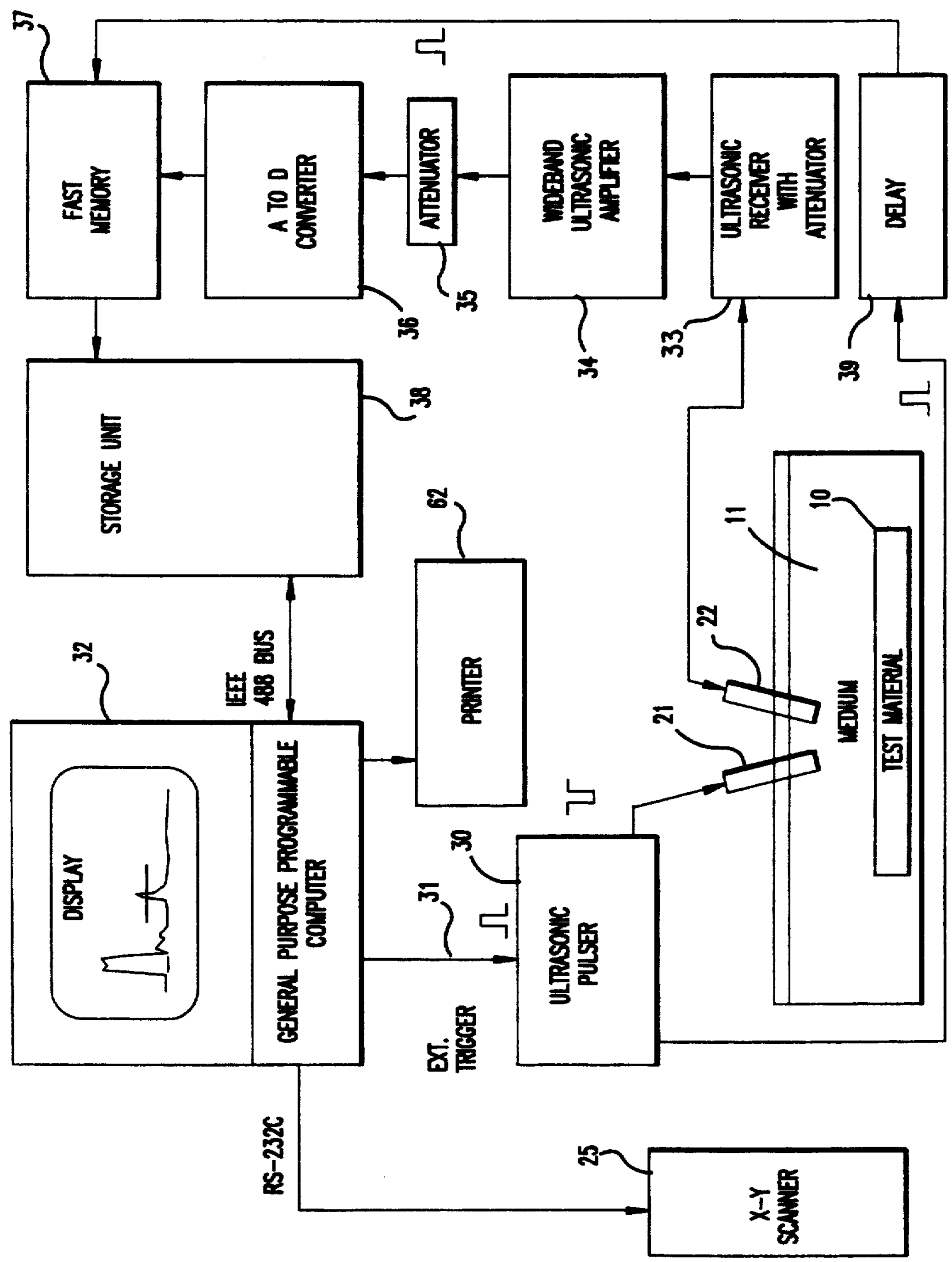
FIG. 1 is a hardware block diagram showing an automated weld flaw detector system according to the present invention.

The remaining hardware to complete a subsurface flaw test system according to this embodiment is shown in FIG. 1. As shown in FIG. 1, the transmit probe 21 is connected to an ultrasonic pulser 30, such as a Metrotek MP 203, which is triggered via a line 31 to the programmable computer 32 by an external trigger output line 31. The signal output of the receive probe 22 is connected to a receiver/attenuator 33, such as a Microtek model MR101, the output of which is connected to an ultrasound wideband amplifier 34. The output of the ultrasound wideband amplifier 34 is attenuated by an attenuator 35, set here at 6 db, and then digitized by an A/D converter 36.

The sample rate of the A/D converter 36 is selected according to the desired flaw detection resolution and the specific ultrasound frequency used. In this embodiment, an A/D 36 having a sample rate of 50 Mhz and resolution of 8 bits was used. The A/D 36 of this embodiment is integral to the general purpose digital storage unit 38, which was a LeCroy Model 8901A transient waveform analyzer. A block of the A/D converter 36 digital output is stored, the length of the block explained below, in a fast buffer memory 37 within a general purpose digital data storage unit 38. The LeCroy model 8901A transient waveform analyzer used as the digital data storage unit 38 for this example contains a fast buffer memory 37.

Referring to FIGS. 1 and 5, timing for the system of this embodiment is referenced against a TrigPulse command output from the computer 32 over line 31. As shown in FIG. 1, the trigger pulse over line 31 is delayed by a delay unit 39. The delay causes the fast buffer 37 to begin capturing samples just prior to receiving samples of the first surface reflection from the test material 11. The delay unit 39 is therefore selected according to the round trip propagation time of sound from the transmit probe 21, to the incident surface of the test material 10, and back to the receive probe 22. More specifically, the delay unit 39 is set, using known sound propagation theory, according to the height h of the probes 21 and 22, their relative distance d, their angle Θ, and the speed of sound through the medium 11. For this embodiment, using the values of H,d, and Θ discussed below, with water being the example medium 11, the delay was set at 120 microseconds.

The number of samples to be captured by the fast buffer unit 37 is set according to the depth of inspection into the test material 10, together with the round trip speed of sound through the test material 10 to that depth and the sample rate of the A/D converter 36. Various methods are known in the art for varying this sample block size, depending in part on the particular hardware implementation of the fast buffer 37. The storage unit 38 of this embodiment, a LeCroy model 8901A transient waveform analyzer, has a feature enabling the user to set the number of samples captured by its component fast buffer unit 37. For this example, as explained in the description of operation below, the sample size was set at 512.

As stated above, the transmit probe 21 and the receive probe 22 are supported within the holder 20 at a distance d/2 from their centerline CL and tilted towards one another at an angle Θ. As also mentioned above, the support 24 must maintain the probes 21 and 22 at a known height H above the test surface. The values for these d/2, Θ, and H parameters are selected as follows:

The height H must be large enough so that the medium 11-to-medium 10 interface is in the far field of the probes 21 and 22. The far field distance is readily obtained from the manufacturer's supplied data. This insures a coherent beam at the surface of the test material 10. So as to maximize the transmission coefficient, H should be just above the far field point. For all embodiments described here H was set at 90 mm.

The value of the angle Θ is selected in accordance with the medium 11-to-medium 10 angle-dependent reflection characteristic. For example, with a water-steel interface, an angle of theta greater than 14 degrees will not permit longitudinal waves to enter the steel. Even 10 degrees is still too sharp, because it results in a longitudinal wave so attenuated after entering the steel, reflecting off of the flaw and returning to the receiving probe 22 that the received flaw signal may have an unusable signal to noise ratio. Therefore, for a water-to-steel interface of the example, a Θ of 5 degrees was selected.

The separation d of the probes 21 and 22 is selected based on the depth of inspection into the test material 10. By referring to FIG. 4, it can be seen that once the angle Θ is set, that the maximum depth of a test volume 14 is determined by the probe spacing d. The test volume 14 is defined as the volume of the test material 10 where the refracted main beam AT of the transmit probe 21 is common to the refracted main beam BT of the receive probe 22. For this embodiment a depth range of 3 to 22 mm was selected. Using a Θ of 5 degrees, as stated above, the d was selected as 21.6 mm.

For the purpose of explaining the operation of the present invention, the test material 10 is shown as having an upper flaw 12 and a lower flaw 13. The sound wave propagation into the medium 10 and the phenomena at each of these flaws 12 and 13 when hit by the ultrasound pulse is described in a summary fashion here. This ultrasound propagation description is not presented as, and is not intended to be, a binding theory. In specific, this sound wave phenomena, as best theorized by the inventors, is as follows:

The pulse from probe 21 proceeds along the main beam A, through the medium 11, which in this example is water, and impinges against the surface of the test material 10. In accordance with known acoustic principles, a percentage of the impinging pulse is reflected back, at the angle of incidence Θ. The portion of the incident pulse which is along an extreme portion Ae of the path A will reflect back along an extreme portion Be of the receive beam B and will strike the receiving probe 22. The apparatus and method of this invention, as described in detail below, detects the received reflection and uses it as a timing reference. The unreflected percentage of the incident pulse undergoes refraction, in accordance with Snell's Law, at an angle α defined in FIG. 4 at the center Al of the beam A, and continues along a diverging path AT into the test material 10. When the refracted incident pulse wavefront strikes the upper flaw 12, an edge reflection occurs first at the upper point **12*a*. As the wavefront continues it strikes consecutive discontinuities along the flaw 12 to the lower point 12*b*. The reflections from these discontinuities can be viewed as consecutive point sources. Since each of the points between 12*a* and 12*b* is within the refracted portion BT of the main beam B of the receive probe 22, a portion of the point source radiations from each will be received by probe 22. Accounting for the delay through the receive probe 22, receiver/attenuator 33, wideband amplifier 34, and attenuator 35, these point source radiations will be sampled by the A/D 36 at respective times corresponding to their depth within the test material 10. When the pulse wavefront which struck the upper flaw 12 strikes the lower flaw 13, a similar reflection results along the discontinuities between the surface of that flaw. As with the upper flaw 12, the reflection from points along the flaw 13 are within the main beam of the receive probe 22 and are sampled by the A/D converter 36 at respective times corresponding to their depth. Because of the pulse angle Θ, as will be explained in paragraph below, the amplitude, as received by the probe 22, of each of the reflections along the discontinuity of flaw 13 will have the same amplitude as those from the flaw 12. Also, as is apparent from FIG. 4, the upper flaw 12 does not interfere with an incident pulse from the probe 21 as it propagates downward to the lower flaw 13 and, likewise, does not interfere with reflections from the lower flaw 13 as they propagate towards the receive probe 22**.

The apparent reason for the echo amplitude, as received by the receive probe 22, being independent of the depth of the flaw from which the echo arrived is as follows: Because of the angle Θ at which probes 21 and 22 are set, and the divergence of the incident beam path A at the respective depths within the test material 10, the incident pulse strikes the upper flaw surface **12*a* with an angle more parallel to the test material face 10 than where it strikes a lower flaw surface, at for example 13*a*. It is theorized that this angle of incidence at the upper flaw surface 12*a* causes an echo with a lower amplitude component in the direction of the receive probe beam than the echo caused by the angle of incidence at the deeper flaw surface 13*a*. As theorized by the present inventors, the larger amplitude of the echo from the deeper flaw surface 13*a* substantially cancels the greater attenuation encountered by this echo. Therefore, even though the flaw echo from 13*a* has a greater attenuation from its longer propagation path than a flaw echo from 12*a*, the two echoes will strike the receive probe 22** with substantially the same amplitude.

The method of operation of this first embodiment will now be described.

Referring to the flow chart of FIG. 5, the computer 32 at step 100 first initializes its scanner position datafile Pos(X(x),Y(y)) according to the starting position of the x-y scanner 25, and at step 101 outputs the corresponding output scanner control signal Scan(x,y). This initial position is referenced as Pos(X(0), Y(0)). The computer 32 at step 102 then outputs a trigger command TrigPulse over line 31. The TrigPulse signal energizes the ultrasonic pulse generator 30 which then energizes the transmit probe 21 to output an ultrasound pulse. The probe 21 and 22 for this example used a center frequency of 5 MHz. This frequency was selected in accordance with the desired 1 mm minimal detectable flaw size, in view of the frequencies available from commercial suppliers. Using the speed of sound in steel, a 5 MHz center frequency was selected, as it provided a 1.2 mm wavelength. The TrigPulse output by the computer 32 is also input to the delay unit 39, delayed 120 microseconds, and then received by the fast buffer unit 37, enabling the buffer to accept a predetermined block of S samples from the A/D 36 through bus 50. In this embodiment, the number S of samples captured for one scan was set at 512, preset via the manual control on the LeCroy model 8901A. The number 512 was selected based on the calculated time difference of arrival, at the probe 22, between the first surface reflection and an echo from the deepest inspection point, 20 mm for this example, within the test material 10. Using a time-of-flight equation (1) defined further below, this time difference was calculated to be 6.38$\mu$ seconds. Dividing this number by the 20 nS sample interval of the A/D 36 of this example, there are approximately 320 samples collected during the 6.38 μS time difference of annual sampling interval. The LeCroy Model 8901A possessed a nearest increment of 512 samples and therefore 512 was chosen.

After the fast buffer unit 37 has stored the S samples, S being 512, the computer 32 receives a BF buffer full signal from the storage unit 38, which is a standard output from the LeCroy Model 8901A, and then proceeds to step 103. At step 103 the 512 samples are loaded into the computer 32 via a standard IEEE 488 interface from the fast buffer unit 37 of the storage unit 38 into a file labelled as S(i), i=1 to S. In this example S=512, as this was the number of samples input to the fast buffer unit 37. Next, at step 104, computer 32 reads the S(i) sample file, beginning at i=1, and compares each read sample against a prestored surface reflection threshold value RT to identify which of the samples corresponds to the first surface reflection received from the test material 10. The specific value of RT is dependent on various hardware parameters, including probe 21 transmit amplitude, receive probe 22 gain, and attenuator 35 setting, but readily obtained by straightforward test. The index i of the first S(i) which exceeds the threshold RT, i.e., the first reference index, identifies that S(i) as S(RT). Alternately, a two-out-three type majority scheme, where two out of three contiguous samples must exceed the RT value, could be used to lessen the chance of error. Based on which of the S(i) samples was determined to be the S(RT) first reflection echo, Step 105 then shifts the sequence S(i) by adjusting the indices of the S(i) file such that S(i) positioned a predetermined number B of samples after S(RT) is given a new index value of i=1, so that S(RT+SKIP) begins the new sequence $S_{shift}$(i), i=1 to 512-SKIP-RT. SKIP is selected according to the number of samples per millimeter and the minimum depth of inspection into the test material 11. In this example the minimum depth of inspection was chosen as 3 mm. This 3 mm value was found to be the minimum depth at which proper operation of this embodiment was observed. Since, the sampling rate of the A/D 36, together with the speed of sound through steel, corresponds to 16 samples per millimeter, SKIP for this example is 16×3 mm=48. Step 106 then parses the $S_{shift}$(i) sequence into C different concatenated blocks, or depth cells, each having D contiguous samples of the $S_{shift}$(i) sequence. In this example there are 16 depth cells, with 1 depth cell per millimeter for depths from 3 mm to 20 mm, and therefore C=16. The number of samples D for each of these blocks is equal to the number of samples per depth cell, which in this example is 16. These blocks contain depth cell data and are labelled as CellData (j,k), with the block number being j=1 to C, here C=16. K references the relative position of a sample within the block, with K ranging from 1 to D, here D=16. Step 107 then finds for each of the C blocks the largest absolute value from among the D samples within that block. These are stored in a file MaxCell(j), j=1 to C. In other words, step 106 finds the largest sample echo from each 1 mm depth range within the test region 14. Alternately, but not shown in this example, Step 107 could be programmed to find for each of the j different CellData (j,k) blocks the average of its D samples and store these accordingly. The program proceeds to Step 108 where each of the MaxCell(i) values is compared against a predetermined flaw echo threshold ET.

The value ET for this example was obtained by gathering a database of sampled echo amplitudes from a test block, placed under the apparatus of the present example, having flaws of various sizes and depths. The present inventors, for this purpose, fabricated a test block having a plurality of tunnel holes, each having a width of 0.3 mm, a height of 3 mm, and each extending the full 19 mm length of the test block, via Electronic Discharge Machining (EDM.). The depth of these tunnel holes, measured to the center of the 3 mm height, ranged from 3 mm to 26 mm below the surface of the block.

During Step 108, each time a MaxCell(j) value exceeds the threshold ET, a value indicating the amplitude of that MaxCell(j) relative to the ET is stored in a file CellHit(x,y,j), where x and y indicate the Pos(X(x)Y(y)) incremental position of the x-y scanner 35, and the j index is given the same value as that MaxCell(j) index. The amplitude of each CellHit(x,y,j) was, for this embodiment, given a value based on the multiples of ET which the MaxCell(j) amplitude represented. In other words, if MaxCell(1) has a value of 3 times ET, and if the x-y scanner 25 is at its Pos(X)(0),Y(0)) position, then a CellHit(0,0,1) having a value of 3 is stored. On the other hand, if MaxCell(1) has a value less than ET then no CellHit(0,0,1) is stored. When Step 108 is complete the CellHit(x,y,j) file is stored onto a suitable capacity storage medium, such as the computer 32 disc drive or its random access memory. Alternately, instead of not storing an entry for CellHit(0,0,1) if MaxCell(1) is less then ET, a value of zero could be stored. This, however, may lead to a data storage difficulty. The reason is as follows: Eventually, as will be obvious from the steps following, the array file CellHit(x,y,j) would have an entry at every location. An integer would indicate an echo received and a zero would indicate no echo received, for each position within the test material 10. However, as will also become obvious from the following steps within this and the other embodiments herein, if the number of increments in the x and y direction is large, such as 1,000 by 1,000, and if the number of CellData(j,k) blocks is equal to 16, for example, then, assuming one byte for amplitude, the CellHit(x,y,j) array file will require 16 megabytes of storage. Since this number is large and since, assuming the ET threshold is set properly, the present inventors found the CellHit(x,y,j) array file to be sparse, only the non-zero values were stored.

Figure 8A:
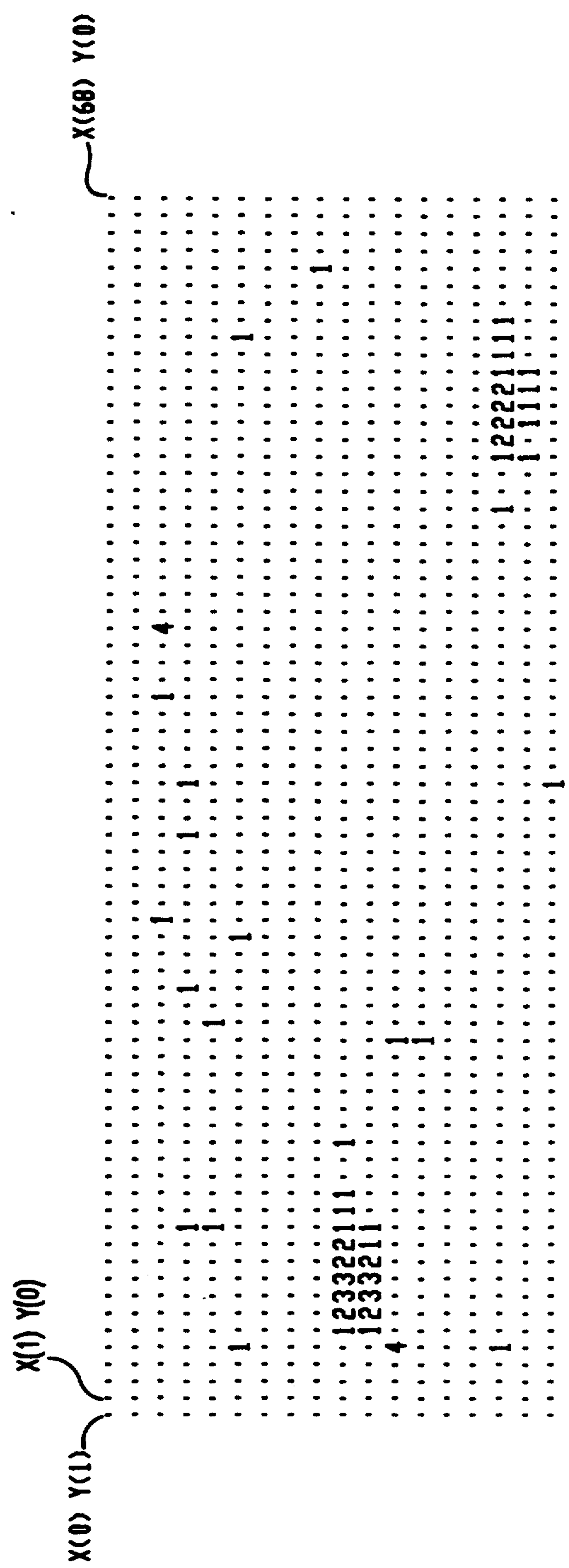
FIGS. 8*a* and 8*b* illustrate a computer video display or print-out of a flaw scan generated by a system according to the present invention.

At step 109 the computer 32 retrieves each CellHit(0,0,j), from the computer 32 disc drive or RAM, and displays on a standard CRT included with the computer 32, or the standard printer 62, the leftmost column X0Y0 shown in FIG. 8a. Since for the example illustrated by FIG. 8a there were no non-zero CellHit(0,0,j) values, the column X0Y0 appears as dots, a dot indicating no entry.

At step 110 the computer increments the x value of the Pos(X(x),Y(y)) scanner position file by 1, and if x is less than a predetermined Xmax, jumps to step 101 which outputs a corresponding signal Scan(x,y) to the scanner 25 and, in response, the scanner 25 increments in the x direction to the Pos(X(1),Y(0)) position. For this example each increment is 1 mm, both in the x and y directions. Steps 102 through 108 are then repeated and at step 109 the computer 32 retrieves each CellHit(1,0,j) and displays the second leftmost column X1Y0 shown in FIG. 8a. In the FIG. 8a example, the column X1Y0 shows non-zero values at the CellHit(1,0,4), CellHit(1,0,10), and CellHit(1,0,15) positions.

Figure 8B:
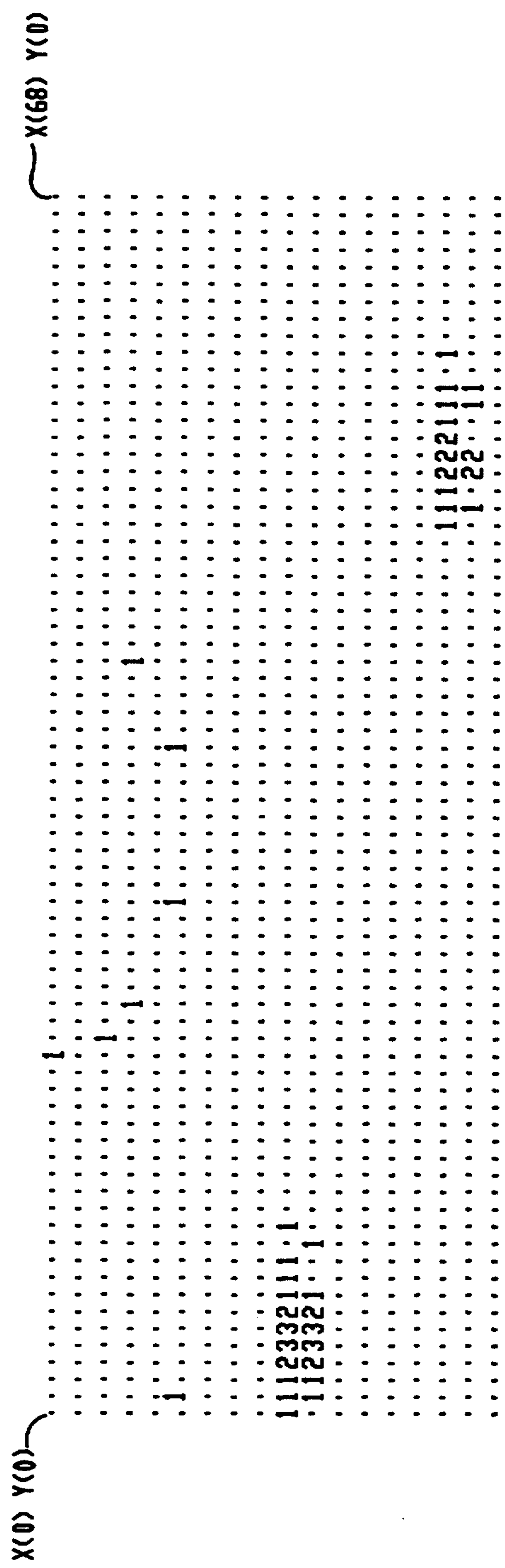

Step 110 is repeated for Pos(X(x),Y(0)) until x=Xmax, at which time the entire scan display of FIG. 8*a* is complete. For this example XMax=68, therefore the rightmost column is X68Y0. The scanner 25 has now traversed the complete length, corresponding to XMax, of the test material 10 in the x direction. At the completion of the step 110 for Pos(X(68)Y(0)), the computer goes to step 111 where the y index of the Pos(X(x-),Y(y)) scan file is incremented by one, and the x index is reset to zero. The scanner 25 at step 101 is then incremented 1 mm, for this example, in the y direction to a position corresponding to Pos(X(0)Y(1)) and then steps 102 through 108 are repeated. At step 109 the computer 32 retrieves each CellHit(0,1,j), and displays the leftmost column X0Y1 shown in FIG. 8*b*. Step 109 is repeated for Pos(X(x),Y(1)) until x=Xmax. At this time the entire scan display of FIG. 8*b* is complete. Step 111 is repeated for Pos (X(x),Y(y)) until y=Ymax. For this example Ymax=1, therefore the scan display of FIG. 8*b* is the final display at the end step 111.

The index value j of a CellHit(x,y,j) entry can be readily converted into a depth into the test material 11 by the following time-of-flight Equation (1):

Equation (1):

$$\text{depth (mm)} = \left[\left(\frac{TOF + 0.33}{0.333}\right)^2 - 6.25\right]^{\frac{1}{2}}$$

Where TOF is a time separation between a time the A/D 36 samples a leading edge of the first surface reflection, and a time the A/D 36 samples an echo energy originating from a flaw corresponding to the CellHit(x-,y,j) entry. Since the sampling interval from the A/D 36 is known, in this example being 20 nS, and there are a known number of samples per CellData(j) block, here being 16, then index number j of the CellHit(x,y,j) entry is directly representative of the TOF time separation. For example, if CellHit(x,y,2) has an entry, then there were 32+B samples in the S(i) sequence between the S(RT) surface reflection and the samples within the CellData(2) block corresponding to CellHit(x,y,2). In this example B was equal to 48 samples, therefore the TOF for CellHit (x,y,2) is 80 samples×20 nS per sample, which equals 1.6μ seconds. For this example, plugging into Equation 1 above, the theoretical depth would be 5.22 mm. Since the CellHit(x,y,j) entries correspond to CellData(j) block having S(i) sample obtained for 1 mm of depth, the 5.22 mm figure would be rounded to 5 mm. Therefore CellHit(x,y,2) would correspond to a flaw surface at 5 mm depth.

Alternatively to plugging the index number j into Equation 1 above, an index j number vs depth table can be readily created by observing the CellHit(x,y,j) entries obtained from a test block, such as the EDM fabricated block described above.

The time-of-flight TOF Equation (1) above was derived as follows with reference to FIG. 4. The derivation depends on two fundamentals: distance equal velocity times time, and the Pythagorean theorem—the hypotenuse equals the square root of the sum of the squares of the sides of a right triangle. The model is:

$$TOF = 2t' + 2t - 2t''$$

where:

$$t'' = s''/C_w = \{[H^2 + x^2]^{\frac{1}{2}}\}/C_w$$

$$t' = s'/C_w = \{[H^2 + (x-L)^2]^{\frac{1}{2}}\}/C_w$$

$$t = s/C_m = \{[depth^2 + L^2]^{\frac{1}{2}}\}/C_m$$

t″ is half the time the surface wave spends in the medium 11 t′ is half the time the sound spends in the medium 11 on its way to the discontinuity t is half the time the sound spends in the material 10 s″ is half the transmission path of the surface reflected wave along Ae and Be s′ is half the transmission path of the sound in the medium 11 to the discontinuity s is half the transmission of the sound in the material 10 to the discontinuity $C_w$ is the longitudinal velocity of sound in the medium 11

$C_m$ is the longitudinal velocity of sound in the material 10

H is the height of the transducers 21 and 22 above the material 10 (stand-off distance)

d/2 is half the separation distance between the transducers 21 and 22

L is half the separation distance between the axes of the transmitting and receiving beams depth is the distance below the interface of a discontinuity.

Plugging in the values of H, d/2, and L used in this example, and the speed of sound through the example medium 11 of water and the example test material 10 of steel and solving for depth yield the Equation (1) shown above.

Second Embodiment

Figure 6:
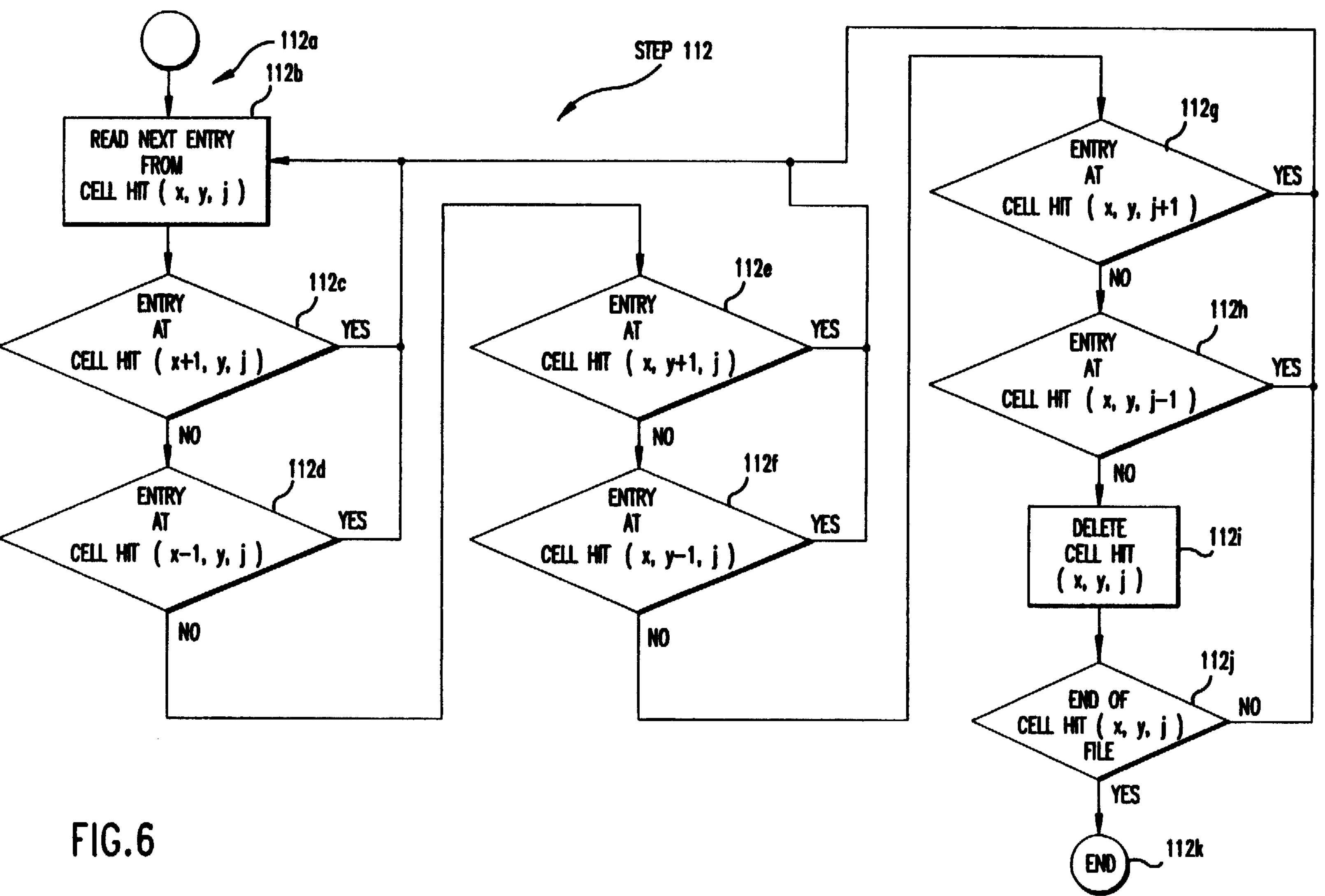
FIG. 6 is a software flowchart showing a noise and data reduction process according to the present invention.
Figure 7:
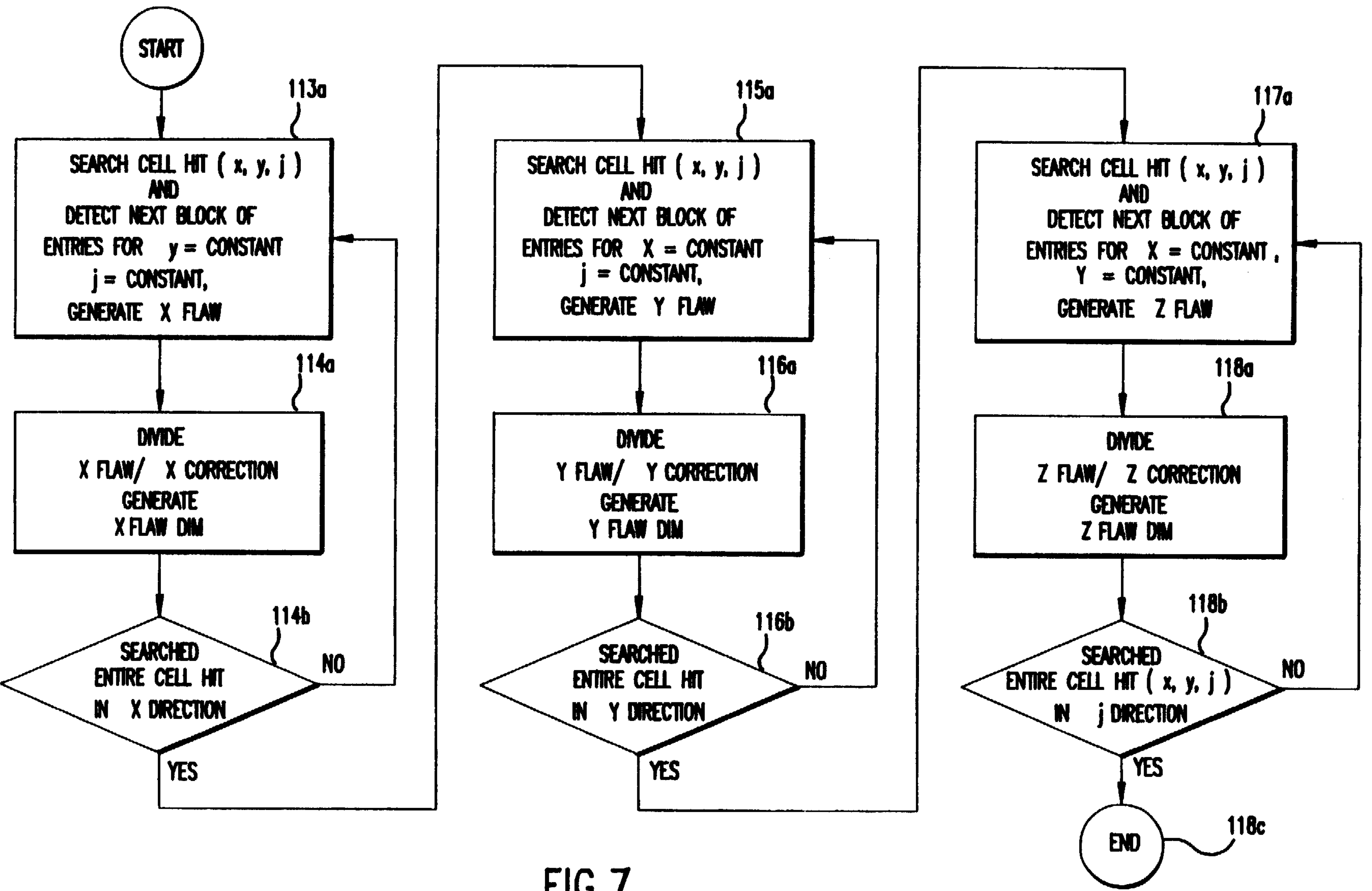
FIG. 7 is a software flowchart showing a 3-dimensional flaw sizing process according to the present invention.
Figure 9A:
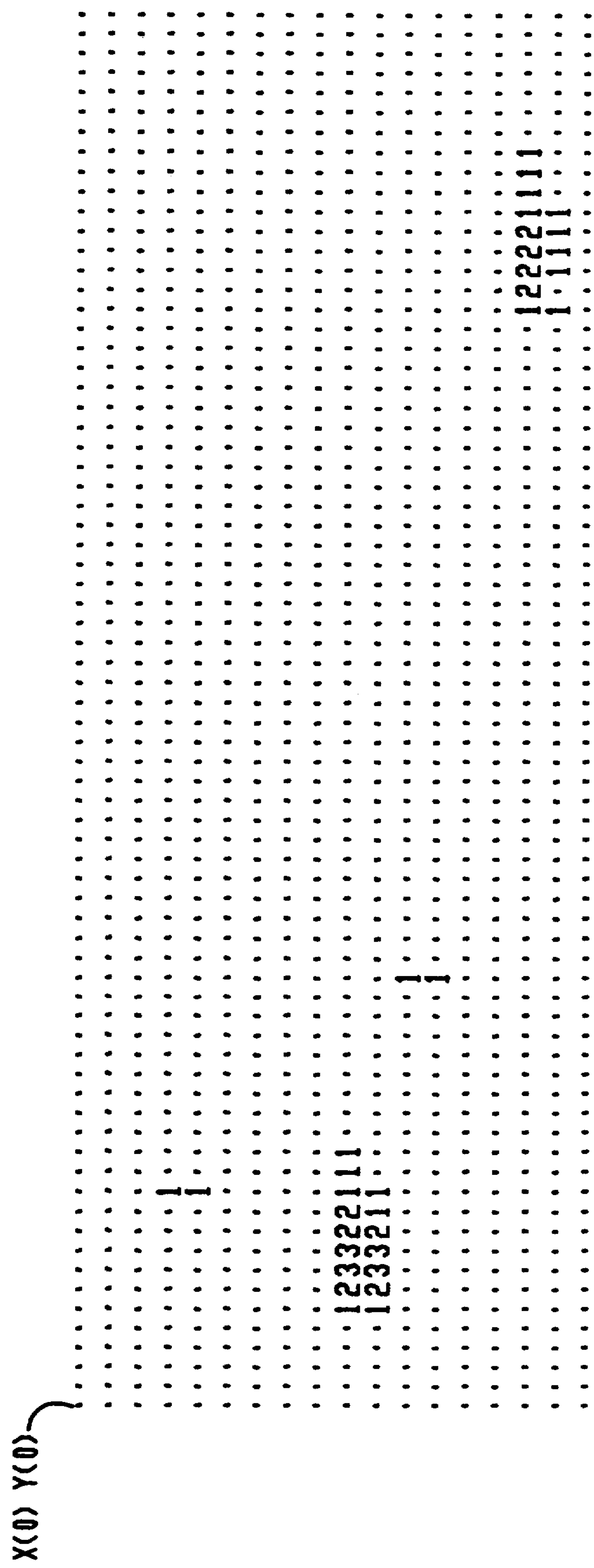
FIGS. 9*a* and 9*b* illustrate a computer video display or print-out of a noise and data reduced flaw scan generated by a system according to the present invention.
Figure 9B:
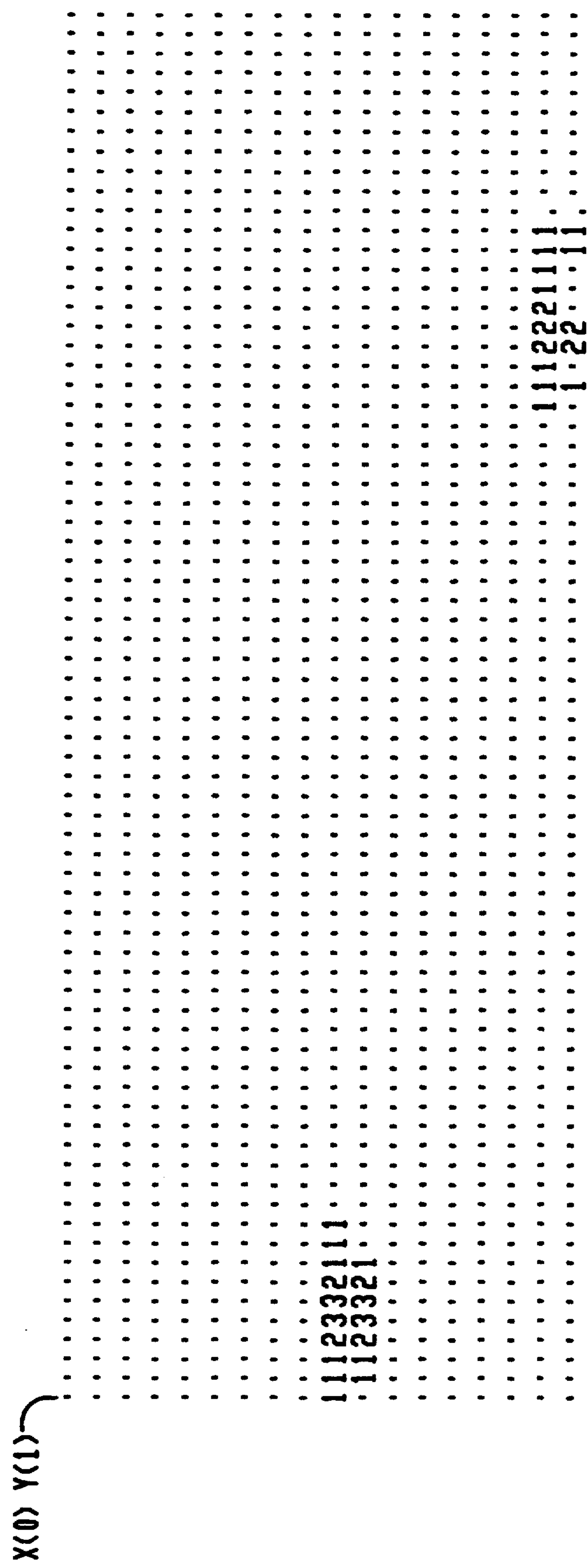

In this embodiment, an additional step 112, as shown in FIG. 6, is performed on the CellHit(x,y,j) array file existing at step 111 to remove single entries of that array file which have no neighbors in either the x, y, or z direction. The need to remove these single entries was discovered by a comparison of CellHit(x,y,j) array files obtained from test blocks, such as the EDM fabricated block described in Embodiment 1, against the tunnel holes within these test blocks, showed that single entries were almost always erroneous. Therefore removing these single entries both lessens the rate of false flaw indications and further reduces the amount of data within the CellHit(x,y,j) array file. The data operations for this step 112 are simple. Basically, for each CellHit(x,y,j) entry, the CellHit(x′,y′,j′) entries are checked, where x′,y′, and j′ are within one unit of the index x,y, and j values respectively. If none of the CellHit(x′,y′,j′) values indicate an entry, then the CellHit(x,y,j) entry is deleted. For example, if CellHit(0,0,1) is non-zero and CellHit(0,0,2) is also non-zero then both of these are saved. However, for the CellHit(0,0,1) entry, if none of CellHit(0,0,0), CellHit(0,0,2), CellHit(0,1,1), and CellHit(1,0,1) are non-zero then that CellHit(0,0,1) entry is deleted. The CellHit(x,y,j) array after reduction by step 112 is labelled as $CellHit_{red}$(x,y,j). FIGS. 9*a* and 9*b* show a display of the $CellHit_{red}$(x,y,j) array file achieved by performing step 112 on the CellHit(x,y,j) array file of FIGS. 8*a* and 8*b*.

Third Embodiment

In this embodiment an additional series of steps are performed on either the unreduced CellHit(x,y,j) of step 111 or the reduced $CellHit_{red}$(x,y,j) array from step 112, which determine the length, width, and height of each flaw corresponding to non-zero entries within these respective arrays. The step will be described as operating on the $CellHit_{red}$(x,y,j) array from step 112 of embodiment 2. There are three pair of steps, 113 and 114, 115 and 116, 117 and 118, and these each operate by walking through the $CellHit_{red}(x,y,j)$ array in the x, y, and j directions, respectively, and for each block of consecutive non-zero entries, counting the number of consecutive entries in that block. The number of consecutive entries are then divided by either an $X_{correction}$, $Y_{correction}$ or $Z_{correction}$ prestored correction factor dimension mapping table, depending on the direction in which the $CellHit_{red}(x,y,j)$ entries are consecutive, and the result is a value indicative of the actual dimension of the flaw. More specifically, step 113 retrieves the $CellHit_{red}(x,y,j)$ array and, holding y and j constant, searches for the first non-zero entry. As an arbitrary example, assume $CellHit_{red}(4,0,0)$ to be the first non-zero entry for y=0, j=0. If the next six entries in the x direction, i.e. $CellHit_{red}(5,0,0)$ . . . $CellHit_{red}(10,0,0)$ are non-zero, then step 113 would generate an XFlaw data word having information indicating 7,0,0 as the x,y,z center of the block and the number 7 representing the size of the block. The program then goes to step 114. The step 114 divides the block size number by the prestored $X_{correction}$ factor and outputs a corresponding XFlawDim data point. The XFlawDim data point indicates the x dimension, or length, of an actual flaw within the test material, echoes from which are indicated by the $CellHit_{red}(x,y,i)$ array obtained from the steps 100 through 110.

The $X_{correction}$ value was previously obtained and stored by placing a test block under the apparatus of embodiment 1, similar to the EDM fabricated block described in that embodiment, and observing the number of contiguous $CellHit_{red}(x,y,i)$ entries, in the x direction, which result from each of the various size known cavities.

The $X_{correction}$ value for this embodiment was determined as follows: First, it should be again noted that each increment of the x-y scanner 25 is 1 mm, in both the x and the y directions. A flaw of 0.3 mm length in the x direction was found to cause, on the average, two contiguous entries, or hits, in the x direction within the $CellHit_{red}(x,y,j)$ array. Therefore a flaw of 0.3 mm length in the x direction was observed for 2 mm of x-direction scanning. It should be noted, that the x-direction is defined here as a direction parallel to the test material 10 face and perpendicular to a line connecting the probes 21 and 22. A flaw of 0.9 mm length in the x-direction was observed to cause, on the average, between 5 and 6 contiguous entries in the x direction within the $CellHit_{red}(x,y,j)$ array. Therefore, it was found, on the average, that a flaw was observed for approximately 6.6 times the actual length of the flaw in the x-direction. Therefore, step 114, by dividing the number of contiguous entries within each block of $CellHit_{red}(x,y,j)$ identified by step 113 by an $X_{correction}$ of 6.6, for this example, provides a close estimate to the actual length of the flaw. The $Z_{correction}$ and $Y_{correction}$ factors for this embodiment were determined in a similar manner.

Steps 115 and 116 operate identical to steps 113 and 114, in that for each block of contiguous $CellHit_{red}(x,y,j)$ in the y direction, step 115 calculates a Yflaw data word, and step 116 divides the y-direction block size indicated by that YFlaw word by a prestored $Y_{correction}$ factor, and outputs a YflawDim data point indicating the width, in the y-direction, of a flaw corresponding to that block. Likewise, steps 117 and 118, for each block of contiguous $CellHit_{red}(x,y,j)$ entries in the z direction, calculate a Zflaw data word, divide the z-direction block size indicated by that word by a prestored $Z_{correction}$ factor, and output a ZFlawDim data point indicating the height, in the z-direction, of a flaw corresponding to that block.

An alternate to steps 113–118 is to map the $CellHit_{red}(x,y,j)$ array onto a prestored reference array, RefArray(x,y,j), containing an experimentally obtained $CellHit_{red}(x,y,j)$ signature for each of a template set of flaws. The mapping or correlation step can be performed by any from among the well known variety of correlation techniques, including sliding window convolution, least-mean-square fitting, and neural network pattern recognition.

Fourth Embodiment

The apparatus and method of this embodiment is identical to Embodiment 1 except that the distance d spacing between the probes 21 and 22 is set at 29.6 mm, for which generates a beam pattern optimized for inspecting depths between 21 mm and 38 mm. The probe holder 60 for this embodiment is shown in FIG. 2a. The operation of a system according to this embodiment is identical in all respects to the Embodiments 1-3 except that step 104, which reads in sequence the S(i) sample file, beginning at i=1, and compares each read sample against a prestored reflection threshold value RT to identify which of the samples corresponds to the first surface reflection received from the test material 10, would detect a reflection from a side lobe of the transmitter probe 21 instead of the main lobe. The reason is that the H of 90 mm, Θ of 5 degrees, with d at 29.6 mm, cause the surface reflection of test material 10 from the main lobe of probe 21 not to be in the beam B of the receive probe 22. Instead, a side lobe signal from the probe 21 is used, as at the d values of H, Θ, and d of this embodiment, it would reflect from the test material 10 into the main beam B of the receive probe 22. This side lobe reflection will be identified at step 104 as S(RT). The RT threshold value may be different than with the previous embodiment.

The present invention has been described in detail in conjunction with and reference to preferred embodiments. It should be appreciated to those of skill in the art that this invention is never restricted to these illustrated embodiments. Numerous modifications and variations of both hardware and software will readily occur to those of skill in the art.

What is claimed is:

1. A method for detecting discontinuities within a material under test, comprising the steps of:

generating an ultrasonic pulse, at a pulse reference time, towards a surface of a material under test, said pulse incident to the surface along a diverging main generating beam of a transmit probe at a beamcenter angle Θ;

receiving a reflected ultrasound energy along a main receiving beam of a receiving probe, a beamcenter of said main receiving beam having an included angle of 2×Θ with said beamcenter of said main generating beam, and outputting a signal corresponding to said received ultrasound energy;

sampling said output signal at a predetermined sampling rate and outputting a corresponding sample data stream;

storing first scan data, consisting of a series of M consecutive datum from said sample data stream over a predetermined interval relative to said pulse reference time, wherein said storing includes storing index data indicating a position of each datum within said series;

retrieving data from among said first scan data and identifying a position of a reference datum within said series;

identifying data points from within said first scan data having an amplitude above a predetermined flaw echo amplitude; and based on a time-of-flight difference between said sampling of said identified data points and said reference datum, generating and outputting first depth cell data, said first depth cell data indicative of a depth dimension to a discontinuity within the material under test.

2. A method according to claim 1 wherein said step of retrieving data from among said first scan data and identifying a position of a reference datum within said series comprises the steps of:

comparing said retrieved data against a predetermined surface reflection threshold value;

based on said comparison, identifying a reference datum corresponding to a first reflection of said ultrasound energy from the surface of the material under test; and generating a first reference index indicating said position of said reference datum within said series.

3. A method according to claim 2 wherein said step of identifying data from within said first scan data having an amplitude above a predetermined flaw echo amplitude comprises the steps of:

parsing said first scan data into N groups, each group being within a position region within said series of M consecutive datum relative to said first reference index, each of said groups being identified by a depth cell index i, with i ranging from 1 to N;

identifying a datum from within each of said N groups having a maximum absolute amplitude value;

comparing said identified datum from within each of said N groups against a predetermined flaw echo threshold value; and generating data indicating each depth cell index i for which the associated group has an identified datum above said predetermined flaw echo amplitude.

4. A method according to claim 1 further comprising the steps of:

determining a correlation between a first and second datum from among said first depth cell data; and generating a height datum, in accordance with said determined correlation, indicative of a height dimension between an upper and a lower portion of a discontinuity within the material under test, said height dimension being in a direction normal to the test material surface.

5. A method according to claim 4 further comprising the steps of:

displacing each of said main generating beam and main receiving beam a predetermined distance in a displacement direction parallel to the test material surface;

repeating said steps of generating, receiving and sampling;

storing second scan data, consisting of a series of M consecutive datum from said sample data stream over a predetermined interval relative to said pulse reference time, wherein said storing includes storing index data indicating a position of each datum within said series;

retrieving data from among said second scan data and identifying a position of a reference datum within said series;

identifying data points from within said second scan data having an amplitude above a predetermined flaw echo amplitude;

generating second depth cell data in accordance with said identified data points;

correlating said second depth cell data against said first depth cell data and generating corresponding correlation data; and based on said correlation data, generating and outputting a planar dimension datum corresponding to a planar dimension of a discontinuity within said test material, said planar dimension being in a direction along said displacement direction.

6. A method according to claim 5, further comprising the step of:

based on said correlation data, deleting data from among one of said first depth cell data and said second depth cell data.

7. A method according to claim 5, further comprising the step of:

displaying said first depth cell data and said second depth cell data in a format having a position information indicating a location and at least one dimension of a discontinuity within the test material, said location and at least one dimension corresponding to said depth dimension, said height dimension and said planar dimension of the discontinuity, said location being within an intersection within said test material of said transmit probe main generating beam and said receiving probe main receiving beam.

8. An apparatus for detecting discontinuities within a material under test comprising:

means for generating an ultrasonic pulse, at a pulse reference time, towards a surface of a material under test, said pulse having a diverging main generating beam incident to the surface at a beamcenter angle $\Theta$;

means for receiving a reflected ultrasound energy, said receiving means having a main receiving beam, a beamcenter of said main receiving beam having an included angle of $2\times\Theta$ with said beamcenter of said main generating beam of said generating means, and said receiving means capable of outputting a signal corresponding to said received ultrasound energy;

means for sampling said output signal at a predetermined sampling rate and outputting a corresponding sample data stream;

means for storing first scan data, said first scan data consisting of a series of M consecutive datum from said sample data stream over a predetermined interval relative to said pulse reference time, said storing means being capable of generating index data indicating the position of each datum within said series;

means for retrieving data from among said first scan data and identifying a position of a reference datum within said series;

means for identifying data points from within said first scan data having an amplitude above a predetermined flaw echo amplitude; and means for generating, based on a time-of-flight difference between said sampling of said identified data points and said reference datum, first depth cell data, said first depth cell data indicative of a depth dimension to a discontinuity within the material under test.

9. An apparatus according to claim 8 further comprising:

means for determining a correlation between a first and second datum from among said first depth cell data; and means for generating a height datum in accordance with said determined correlation, wherein said height datum is indicative of a height dimension between an upper and a lower portion of a discontinuity within the material under test, said height dimension being in a direction normal to the test material surface.

10. An apparatus according to claim 8 wherein said means for retrieving data from among said first scan data and identifying a position of a reference datum within said series comprises:

means for comparing said retrieved data against a predetermined surface reflection threshold value and, based on the comparison, identifying a reference datum corresponding to a first reflection of said ultrasound energy from the surface of the material under test; and means for generating, based on said identified reference datum, a first reference index indicating said position of said reference datum within said series.

11. An apparatus according to claim 10 wherein said means for identifying data from within said first scan data comprises:

means for parsing said first scan data into N groups, each group being within a position region within said series of M consecutive datum relative to said first reference index;

means for identifying each of said groups by a depth cell index i, wherein i ranges from 1 to N;

means for identifying a datum from within each of said N groups having a maximum absolute amplitude value;

means for comparing said identified datum from within each of said N groups against a predetermined flaw echo threshold value; and means for generating, based on said comparison, data indicating each depth cell index i for which the associated group has an identified datum above said predetermined flaw echo amplitude.

12. An apparatus according claim 9 further comprising:

means for displacing each of said main generating beam and said main receiving beam a predetermined distance in a displacement direction parallel to the test material surface;

means for storing second scan data, consisting of a series of M consecutive datum from said sample data stream over a predetermined interval relative to said pulse reference time, said storing means being capable of generating index data indicating the position of each datum within said series;

means for retrieving data from among said second scan data and identifying a second reference index position of a reference datum within said series;

means for identifying data points from within said second scan data having an amplitude above a predetermined flaw echo amplitude;

means for generating second depth cell data in accordance with said identified data points;

means for correlating said second depth cell data against said first depth cell data and generating corresponding correlation data; and means for generating and outputting, based on said correlation data, a planar dimension datum corresponding to a planar dimension of a discontinuity within said test material, said planar dimension being in a direction along said displacement direction.

13. A apparatus according to claim 12, further comprising:

means for deleting, in accordance with said correlation data, a data from among one of said first depth cell data and said second depth cell data.

14. An apparatus according to claim 12, further comprising a means for displaying one of said first depth cell data and said second depth cell data in a format having a position information indicating a location and at least one dimension of a discontinuity within the test material, said location and at least one dimension corresponding to said depth dimension, said height dimension and said planar dimension of the discontinuity, said location being within an intersection within said test material of said main generating beam and said main receiving beam.

* * * * *